US008355692B2

(12) United States Patent
Ricordi et al.

(10) Patent No.: US 8,355,692 B2
(45) Date of Patent: Jan. 15, 2013

(54) SYSTEM AND METHOD FOR TRANSMITTING USER DATA RECEIVED BY AN AUTHORIZED APPROVER

(76) Inventors: Camillo Ricordi, Miami, FL (US); Steven Sikes, Miami, FL (US); Stephen William Anthony Sanders, Sebastopol, CA (US)

( * ) Notice: Subject to any disclaimer, the term of this patent is extended or adjusted under 35 U.S.C. 154(b) by 200 days.

(21) Appl. No.: 12/834,848

(22) Filed: Jul. 12, 2010

(65) Prior Publication Data
US 2011/0021172 A1    Jan. 27, 2011

Related U.S. Application Data

(60) Provisional application No. 61/224,468, filed on Jul. 10, 2009.

(51) Int. Cl.
*H04M 11/04* (2006.01)

(52) U.S. Cl. ............... 455/404.1; 348/231.99; 705/14.4

(58) Field of Classification Search ............... 455/404.1; 705/44, 14, 26, 18, 14.4; 709/206; 348/231.99
See application file for complete search history.

(56) References Cited

U.S. PATENT DOCUMENTS

| | | | |
|---|---|---|---|
| 2009/0055319 A1* | 2/2009 | Raheman | 705/44 |
| 2009/0182630 A1* | 7/2009 | Otto et al. | 705/14 |
| 2010/0145737 A1* | 6/2010 | Joao | 705/4 |

* cited by examiner

*Primary Examiner* — Phuoc Doan

(57) ABSTRACT

This present invention relates to a system, method, and apparatus for an authorized approver (AA) to receive and transmit information to contacts of an end user or others. The authorized approvers may receive, for example, voice, data or video or a combination thereof from the end user. Said authorized approver may view the received information on a back-end server or on a telecommunications device including but not limited to a mobile device or mobile internet device. The authorized approvers may retransmit the end user data to one or more contacts of the end user. Before such retransmission, the authorized approver, may amend, summarize, modify, tag, or otherwise edit the end user information before sending it on to the end user contacts.

18 Claims, 3 Drawing Sheets

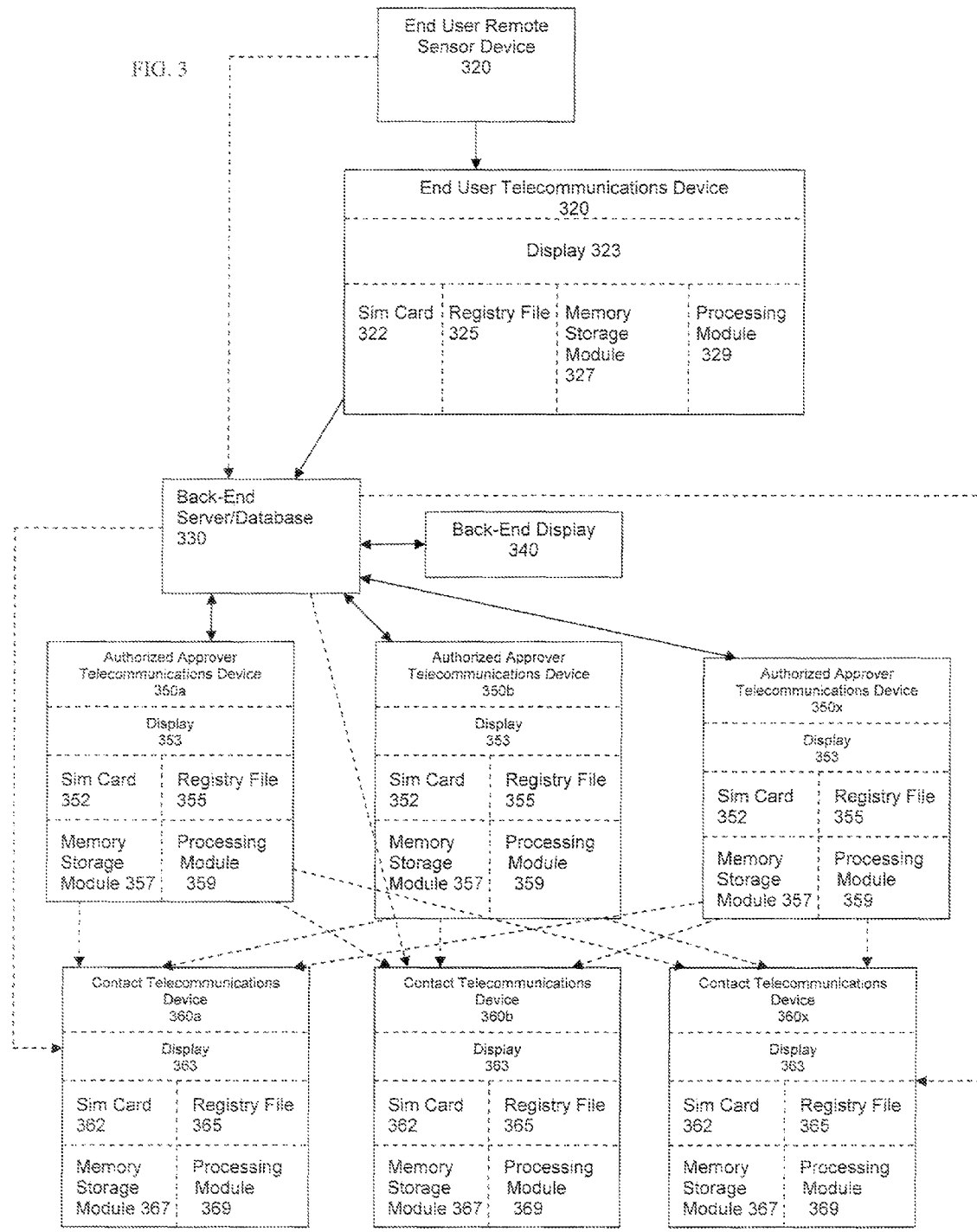

SYSTEM AND METHOD FOR TRANSMITTING USER DATA RECEIVED BY AN AUTHORIZED APPROVER

This application claims priority to U.S. Provisional Patent Application No. 61/224,468, filed on Jul. 10, 2009, which application is incorporated by reference in its entirety.

FIELD OF THE INVENTION

The present invention is in the field of telecommunications. More particularly, disclosed is a system and method for an authorized person to receive, approve and transmit data to contacts.

BACKGROUND OF THE INVENTION

It is desirable for authorized approvers ("AA") to be able to process voice, data and video (VDV) received from end users and to review the importance of such incoming voice, data, or video transmissions. Often, voice, data, or video information may be created and/or transmitted by or on behalf of end users that is vital to the end user's health or well being, such as if an end user has an emergency situation and signals such emergency by pressing an emergency button, or if the end user has an emergency situation that is identified to remote locations by transmitting voice, data or video that contains other vital information including but not limited to physiological data, location data or other informational readings. The signal, whether sent by pressing an emergency button or through the transmission of VDV, may be sent directly from a telecommunication device ("TD") such as a cell phone. Further, these signals and/or VDV information may be received by an authorized approver (AA), such as a doctor or other medical care provider, who may then transmit the signal or information to authorized contacts, such as family members of the end user in distress.

It is desirable for authorized approvers (AA) who receive any such emergency transmissions from end users to have a system, method and apparatus to be able to review the VDV transmitted by or on behalf of the end user from a telecommunications device (TD). An authorized approver may include but not be limited to a physician or medical care provider, and the ability to receive VDV originated from a end user on a TD may save time, and may shorten the timeframe in which the VDV may be reviewed and subsequently retransmitted and/or amended and retransmitted to one or more contacts of the end user, or other contact, at the discretion of the authorized approver.

Systems and methods currently exist that enable AAs to receive end user emergency signals indicating. However, existing methods and systems have various disadvantages. First, the existing systems and methods described above are typically not mobile, in that they do not send the actual VDV information to the telecommunications device (TD) of an AA, nor do they easily allow for easy "one-button" or "single action" release or retransmission of VDV to one or more contacts of the end user, or other contact or contacts. Existing inventions do not indeed allow vital VDV to be retransmitted in real-time to contacts of the end user or other contacts who may be positioned to aid the end user in cases, including but not limited to, a medical emergency.

Many types of critical events, such as medical, health and personal emergencies, may be addressed and/or alleviated with prompt medical attention and rescue intervention. For example, subjects having hypoglycemic episodes may simply need a glass of orange juice or a glucagon tablet to elevate their blood sugar. In children or the elderly, the time for response may be more critical, and these subjects may not be able to provide the needed self-assistance or may not be cognizant or may not be in the position to ask someone for help due to their medical condition or the severity of a critical event. Further, because the onset of many emergency medical conditions is gradual, the subjects and those in the vicinity of the subjects experiencing a critical event may not recognize the imminent danger and potential risk.

Also, many health emergencies go untreated until permanent physical damage or death occurs, even when someone is in the vicinity, because that person was not aware or was not alerted of the critical event. Further, if an individual was to recognize that a subject needed assistance, the individual may not know how to care for the subject in distress. Further still, emergency personnel may take several minutes to assess the critical event before administering the correct or appropriate treatment. Each delay may lead to increased permanent physical damage, unnecessary suffering, extreme trauma or even death.

Therefore, there is a need in the industry for more efficient system and method for allowing AAs who receive emergency or distress signals with VDV information from end users to immediately receive and distribute such signals or VDV information on to authorized contacts of the end user from whom the signal and/or information originated.

SUMMARY OF THE INVENTION

In one embodiment, an authorized person (also referred to as an authorized approver) may receive data from an end user including but not limited to voice, data, video, positioning coordinates, location on a map or physiological data (collectively or individually referred to as "user data" or "user information"). The authorized person may view the user information on a backend information technology platform or on a telecommunications device (TD) including but not limited to a mobile interne device or mobile phone (MID). The user information may be transmitted by the authorized person to one or more contacts, including but not limited to designated contacts of the end user from whom the user information originated, or another approved or designated contact. The authorized person may amend, tag, note and/or retransmit the user data. The authorized person may retransmit voice, data, video or other user data to contacts of an end user, or to other parties.

The invention allows for an authorized approver to receive and retransmit voice, data or video (VDV) to contacts of an end user comprising: providing a module comprising; a graphical user interface for displaying captured voice, data or video objects on a display on a back-end information technology system; a telecommunications device (TD) module of the end user operably connected to one or more remote sensor devices (RSD) to capture voice, data, or video (VDV); a one or more remote sensor devices modules for capturing VDV from an end user; code for registering an end user, authorized approvers and contacts of end users and other contacts; code for registering information including location coordinates; registering an end user; registering a contact of end user or other contact; registering an authorized approver; capturing the voice, data and video of end user; displaying voice, data and video of end user on a back-end system; displaying voice, data and video of end user on an authorized approver's telecommunications device; tagging, amending or attaching messages by authorized approver to voice, data and video of end user; transmitting by authorized approver the voice, data, video of end user with or without tags, amendments or messages from authorized approver to contacts of end user or to the telecommunications devices of contacts of end users or others; wherein the module, the telecommunications device module of end user, the back-end display, the telecommunications device of the authorized approver, the remote sensor device (RSD) of the end user, the telecommunications devices of the contacts of the end user or other contacts are all operably connected. The above-mentioned devices may all contain software in order to facilitate their intended functions. The software may be similar or different, since the TD's can be different. However, each device can interoperate and communicate in order to provide a working end-to-end solution.

Other systems, methods, features, and advantages of the present invention will be or will become apparent to one with skill in the art upon examination of the following figures and detailed description. It is intended that all such additional systems, methods, features, and advantages be included within this description, be within the scope of the invention, and be protected by the accompanying claims.

BRIEF DESCRIPTION OF THE DRAWINGS

The invention may be better understood by referring to the following figures. The components in the figures are not necessarily to scale, emphasis instead being placed upon illustrating the principles of the invention. In the figures, like reference numerals designate corresponding parts throughout the different views.

FIG. 3 depicts an illustration of the system of the invention.

DETAILED DESCRIPTION OF THE INVENTION

Figure 1:
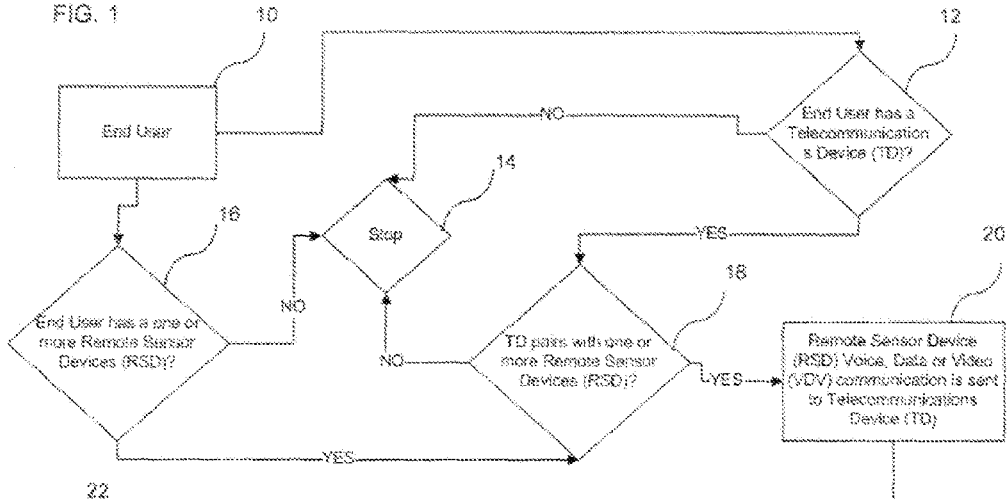
FIG. 1 depicts an illustration of the method of the invention.
Figure 1:
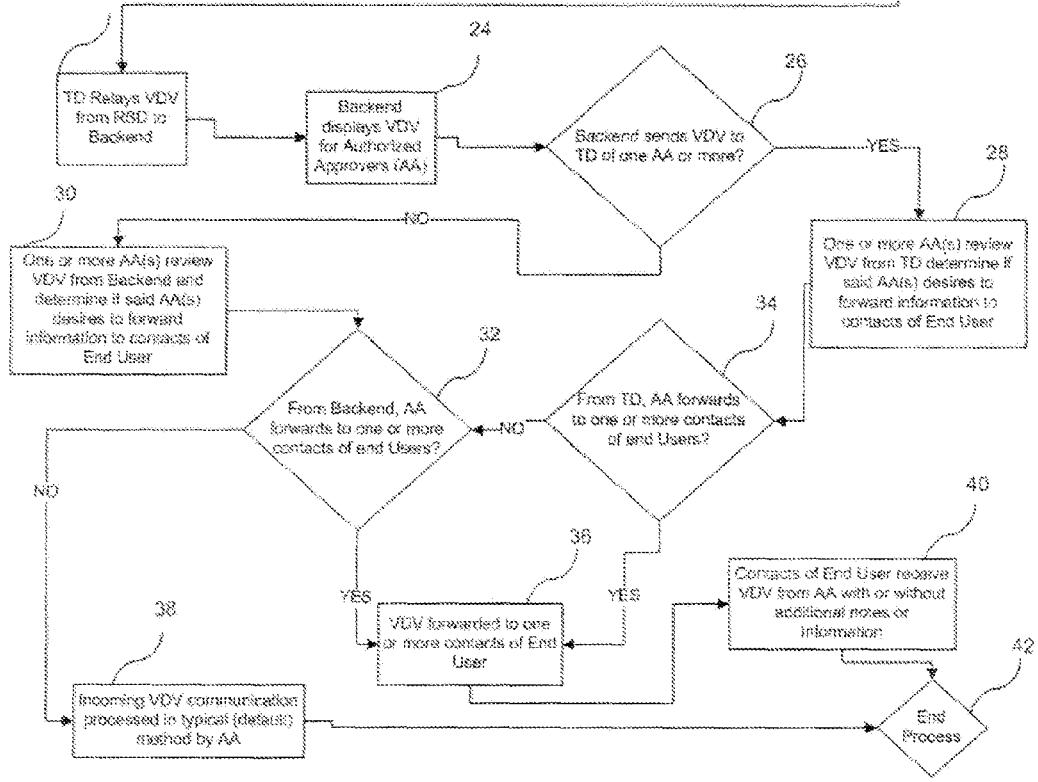

The present invention relates to a system, method and apparatus to facilitate capturing and reviewing data in a timely manner. The data, namely voice, data, and video (VDV) may include a plurality of types of information that may be sent to the authorized approver so that if the data is information that is immediately actionable, it can be acted upon in an approved manner. For example, an interstitial blood glucose reading that is dangerously low, may cause an authorized approver to call 911, and also retransmit the information to one or more contacts of the end user or other contact that may be close enough to immediately aid the end user to mitigate risk.

Another example may be an oxygen saturation level that is dropping very quickly, and in which case, as authorized approver may be able to view this information from their respective TD and to retransmit the data to a contact of the end user, who may be able to immediately aid the end user. Other VDV can be received from remote sensor devices (RSDs) that read data including but not limited to interstitial blood glucose, ECG, EKG, pulse, oxygen saturation, respiratory rate, push-button alert, and spoken alert and other data.

The VDV can be transmitted automatically from an end user's remote sensor device to the end user's TD without the end user taking any action. The RSD can read physiological data levels from the end user's RSD, including but not limited to, interstitial blood glucose, ECG, EKG, pulse, oxygen saturation, respiratory rate. Moreover, the VDV can be transmitted by the end user to a respective end user's TD by the end user performing an action including, but not limited to, pushing a button to send an alert, speaking an alert, or other data-transmitting action, to the RSD and/or directly to the TD, or a combination thereof. Ultimately, the data from the end user's RSD is sent to the end user's TD, and the data from the end user's TD, whether it comes originally from the RSD or from the end user's TD itself, is sent to the one or more authorized approvers via a back-end system. From the back-end system the data may be sent to other authorized approvers who are in a remote location. Alternatively, the end user data may be sent directly to predetermined authorized approvers without going through a back-end server. In such a situation, the authorized approvers would receive the information on a TD having processing functionality and capability similar to that of the back-end server, as appropriate.

The end user does not need to activate an RSD, such as by physically pushing a button. Rather, the RSD may be configured to activate automatically upon detecting certain physiological or other conditions being experienced by the end user. An example of automatic activation would be a pulse oximeter as an RSD, which is configured to send data to the end user's TD, and to trigger an alert if an oxygen saturation level drops below a certain percentage. Typically, the RSD can send the end user's TD signals that contain the physiological data levels of the end user. The signals can be sent by means including, but not limited to voice, text, e-mail, and video. The physiological data levels of an end user can include, but are not limited to, pulse, oxygen saturation level, respiratory rate, temperature, interstitial glucose, ECG data, EKG data, and other data signals. Further, the physiological data can also include any data or information that may help provide actionable information that can help mitigate a prospective emergency or dangerous condition. Other information that can be transmitted includes, but is not limited to, physical location, velocity, and or other geographical data.

The present invention may further be configured to allow the end user's, the approved authorizer's, and the contact's TDs to be active on a network either on a constant basis, an intermittent basis, or some other predetermined timing. For example, any of the TDs may be always on, or checking for signals every 30 seconds, or every 1 minute, or other preselected time interval. The present invention can also be configured to allow a TD to wake-up and to receive and send the VDV, even if the TD is currently inactive or in sleep mode. The RSD can send a signal, as described above, that a TD can recognize, and then wake itself up, if the device has been pre-configured to do so. The end user's TD may transmit to the back-end system through various networks including, but not limited to, mobile networks (CDMA, GSM and others) local networks (WiFi, WiMax, and others) wired Internet Protocol networks and wireless Internet Protocol networks.

In one embodiment, data from one or more end users may be able to be reviewed by one or more authorized approvers on a back-end system that displays data on a PC, webpage or other graphical user interface ("GUI"), in addition to, or instead of, on a GUI of the authorized approvers' TDs. The received VDV can be viewed via a graphical user interface. The back-end system can be a central server or hub where authorized approver can view or otherwise inspect the VDV. For example, the central server may be located at a hospital, police station, tire department, or an emergency call center. The back-end system may be configured to receive the VDV from the end user and transmit the VDV to the authorized approvers, who may then transmit all or part of the VDV (either in original or edited format) to the end user's contacts after AA review, amendment, and/or modification, as further explained herein. The back-end system has the capability to transmit the data to a remote AA, as well as to a remote contact, by way of the various abovementioned networks and other networks. Alternatively, the VDV may be transmitted directly to the AA(s) without having to go through a central hub.

One example implementation of an embodiment of a method in accordance with the present invention is shown in FIG. 1. First, an end user is provided with a telecommunications device 12 and a remote sensor device 16. The RSD may be incorporated in the TD or may be separate from the TD. If the end user 10 does not have both devices, the method can end 14. Next, the user's telecommunication device pairs with the end user's remote sensor device 18, and VDV or other user data obtained from or through the remote sensor device is acquired by or sent to the end user's TD 20. The end user's telecommunication device 12 may then transmit the VDV or other user data to the back-end server 22, where the information may be displayed on a GUI at the back-end for an authorized approver 24. Alternatively, or in addition to displaying the VDV at the back-end display for authorized approvers 24, the VDV may then be sent to one or more authorized approver remotely via the back end. As shown at steps 28 and 30, one or more AAs may review the VDV or other under information from their own remote TDs (step 28) and/or from the backend display (step 30) if available. Either way, the AAs reviewing the VDV may communicate amongst each other via the system, and/or transmit the relevant information to selected end users (either modified or unmodified).

The information can then be sent to one or more end user contacts 32,34. When transmitted to one or more end user contacts in steps 32,34, the AA(s) may modify, add to, summarize, amend, tag or otherwise edit the information before forwarding it on to the end users 36. Alternatively, the authorized approver can make a decision not to forward the information to any contacts, wherein the information would simply be processed or stored per some default instruction 38. For example, the information may simply be logged and stored in a database on the back end and/or in a storage module of the TD. Or the information may be sent to a storage server remote from either the back-end or the AA's TD. The contacts of the end user receive the information 40 per the AA's instructions and/or edits, and the process is completed 42.

Figure 2:
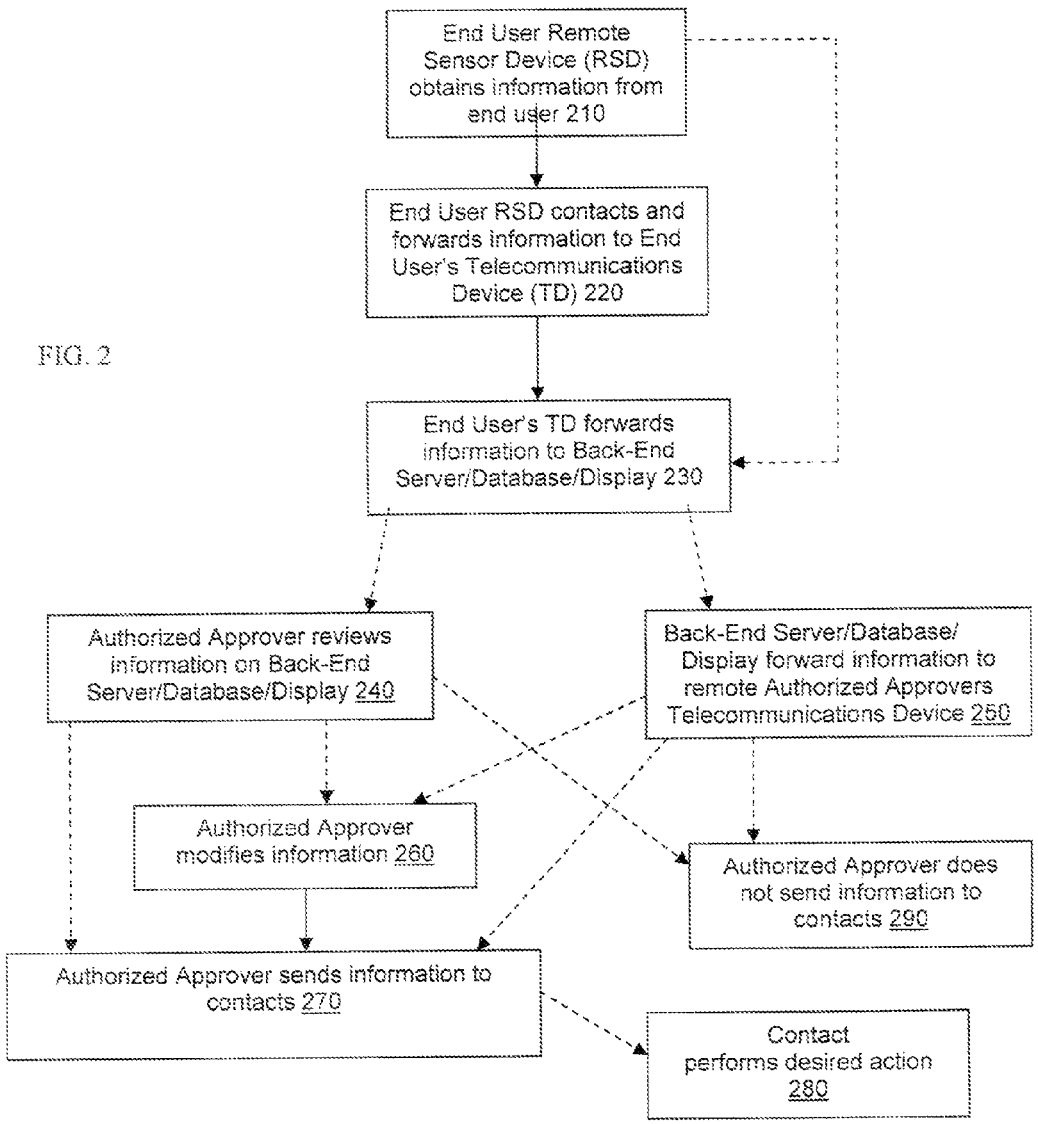
FIG. 2 depicts a second illustration of the method of the invention.

FIG. 2 depicts an alternate implementation of an embodiment of a method in accordance with the invention. Here, an end user is provided with a remote sensor device, which obtains data from the end user 210. This data or information is then sent to the end user's telecommunication device 220, which then sends the information to a back-end server/database/display 230. Alternatively, the RSD may be configured to send the acquired data directly to the back end, without going through a TD. Once received by the back end server 230, An authorized approver can view the information at the back-end display 240. Simultaneously, the information can be sent from the back end server to one or more authorized approver's telecommunications devices remotely 250. Whether at the back end server or through a remote TD, the authorized approvers may modify, add to, summarize, amend, tag, append information to, or otherwise edit the data obtained, from the end user 260. The authorized approver can then, if desired, forward the information (modified or not) to the contacts of the end user 270. If desired, the contact can perform any instructions sent by the authorized approver 280 (such as, for example, going to provide the end user with medication as recommended). Alternatively, the authorized approver may decide not to forward the information to the end user's contacts 290.

A list of authorized approvers can be maintained in a database at the back-end, on a telecommunications device (of the end user and/or the authorized approver(s)), a remote database that is operably connected to the system via any available networking system, or combination thereof. The system can query the database to identify an updated list of authorized approvers. The authorized approver(s) may vary from territory to territory based upon local, state, or national regulations, or other legal logic or frameworks. Typically, a medical doctor or an emergency medical technician with legal access to an end users medical records and history could be an AA. Typically, contacts may include a wider degree of people, including but not limited to neighbors, family, travel partners, care givers and others.

Contacts do not need to be in physical proximity to the end user; however, if a contact is in proximity to an end user it may greatly help to provide assistance and example including but not limited to a father waking up his child in the event of a dangerously low interstitial glucose reading from an RSD during the middle of the night. The disclosed system facilitates programmability and reprogrammability, including but not limited to AA's, contacts, VDV data levels, location data, and more. The end user may program and reprogram system, if they are holders of account ownership. Safeguards are built into the system including but not limited to: end users may not delete all AA's and/or contacts; various rules exist to assure children, the elderly and others at greater risk cannot program or reprogram the device or system.

Components of the system include (as seen in FIG. 3): the end user's RSD 310; the end user's telecommunication device (TD) 320; the back-end server/database 330; the back-end display 340; the authorized approver's remote TD $350_a$; $350_b$; $350_x$; and the contact's TD $360_a$; $360_b$; $360_x$. The back-end server preferably includes a memory storage module for storing the end user data and other pertinent information relating to the end users and their contacts; and a processor for processing the VDV received from the end user as required. The end user's telecommunications device 320 can contain a SIM card 322 or a registry file 325, which are able to control the system's functions and run the software that enables the communication between the parties. In addition, each of the telecommunications devices 320, 350, 360 may also contain a SIM card 322, 352, 362, a registry file 325, 355, 365, a memory storage module 327, 357, 367, a display 323, 353, 363 and/or a processing module 329, 359, 369. If the end user has more than one AA and/or more than one contact, then the system can contact the AAs simultaneously, sequentially or both. An AA can send the data/instructions/amended information to the contacts simultaneously, sequentially or both. If an AA and/or contact TD is not available, or if a response is not received by the back-end within a pre-configurable amount of time, then other AAs and or contacts may be notified.

In accordance with the present invention, the RSD may be, without limitation, a sensor for: interstitial glucose, blood glucose, ECG, EKG, respiratory rate, pulse, blood pressure, peak flow, push-button alert, spoken alert, or oxygen saturation level. And the VDV may include data from an operably connected RSD, GPS or location or mapping data, voice, images or video. Further, as explained, the VDV may be displayed on a back-end system to one or more authorized approvers, and/or on a TD to one or more authorized approvers (AA).

In an embodiment of the disclosed system and method, one or more AAs may decide to send VDV received by a user in original or edited, amended or messaged attached form to one or more contacts of the end user or other contacts by way of a single action such as a push button or by way of multiple actions. In addition or alternatively, sending of the VDV to one or more contacts of the end user, which may include non-specific third parties (such as the local police or local hospital as determined based on the position of the end user) can also begin and open a communication session in which the AA and the user's contacts (or other third parties) are actively engaged in communication by use of back-end displays and/or TDs. In addition or alternatively, the disclosed system and method may employ a software application residing on a TD of the user, AA, or user contacts that may further reside in a registry file or on a SIM card and may employ the opening and start of the application from a signal sent from the RSD, or a single or multiple action taken on the user's TD.

In the present invention, any of the TDs may be configured to receive data from an RSD, and to then verify if the received data signals the operating system of any of the TDs to communicate with SIM card and/or registry file of the TD. This can then activate the TD to take specific measures including, but not limited to, open a software application and to run it in a specific mode such as a normal or emergency mode; send an emergency signal to a back-end; close other unnecessary programs; or restart the TD in a certain or specified mode. This can be, but is not limited to, a normal operational mode or emergency mode. A signal from an RSD can cause the operating system of the TD to query the registry file 325, 355, 365 and/or SIM card 322, 352, 362 of such TD. If a specific file relating to the present system is located and identified, then the registry file 325, 355, 365 and/or the SIM card 322, 352, 362 can open the file, which in turn can cause a software application to open. The application may reside on the TD's memory, in the registry file 325, 355, 365, or on the SIM card 322, 352, 362. This can allows other applications that reside on or in the TD to be closed. Subsequently the application of the present system can be opened by a signal send from the RSD to the TD. This step differs from normal or regular use of how registry files and/or SIM cards function on TDs today, since SIM cards and registry files typically only hold information such as a list of phone numbers. It will be understood by a person of ordinary skill in the art that any of the processing done by the TDs or the backend server 330 would be done by their respective processors 329, 359, 369.

As would be understood by one of ordinary skill in the art having the present description before them, an apparatus of the present invention may include: a telecommunications device (TD) of the end user operably connected to one or more remote sensor devices (RSD) to capture voice, data, or video (VDV); one or more remote sensor devices modules for capturing VDV from an end user; a back-end information technology display; an authorized approver's telecommunications device; a contact of end user's or other contacts' telecommunications device. The connections and operability of these components would be understood by one of skill in the art based on the foregoing description of the method and system. In such an apparatus of the present invention, the RSD may be any known sensor applicable to the current method and system, including by way of example only, sensors for interstitial glucose, blood glucose, ECG, EKG, respiratory rate, pulse, blood pressure, peak flow, push button alert, spoken alert, or oxygen saturation level. As previously explained, the VDV obtained, processed, stored sent and/or received by the apparatus may include, without limitation, data from an operably connected RSD, GPS or location or mapping data, voice, images or video. In one or more embodiments, the VDV may be displayed on a back-end system and/or a MID or other TD, to one or more authorized approvers.

As previously explained, one or more AAs may receive and then review the VDV, and one or more of such AAs may determine whether to amend, edit or add messages to said VDV before transmitting the VDV (or an amended version thereof). The original or edited, amended or messaged VDV may be transmitted to one or more selected contacts of end users (including other contacts such as local hospital or police) by way of a single action such as a push button or by way of multiple actions, and such transmission of VDV by an AA may operate to begin and open a communication session in which the AA and one or more of the contacts are actively engaged in communication by use of back-end displays and/or TDs. In one embodiment of the apparatus, a software application may reside on a TD of the user, AA, and/or contacts, wherein such software may further reside in a registry file 325, 355, 365 or on a SIM card 322, 352, 362 and may employ the opening and start of the application from a signal sent from the RSD, or a single or multiple action taken on said TD to facilitate said apparatus to function in the spirit of this invention.

The foregoing description and drawings merely explain and illustrate the invention and the invention is not limited thereto. While the specification in this invention is described in relation to certain implementation or embodiments, many details are set forth for the purpose of illustration. Thus, the foregoing merely illustrates the principles of the invention. For example, the invention may have other specific forms without departing from its spirit or essential characteristic. The described arrangements are illustrative and not restrictive. To those skilled in the art, the invention is susceptible to additional implementations or embodiments and certain of these details described in this application may be varied considerably without departing from the basic principles of the invention. It will thus be appreciated that those skilled in the art will be able to devise various arrangements, which, although not explicitly described or shown herein, embody the principles of the invention and, thus, are within its scope and spirit.

What is claimed is:

1. A system and method for an authorized approver to receive and retransmit voice, data or video (VDV) to contacts of an end user comprising:
    providing a module comprising
        a graphical user interface for displaying captured voice, data or video objects on a display on a back-end information technology system;
        a Telecommunications Device (TD) module of the end user operably connected to one or more Remote Sensor Devices (RSD) to capture voice, data, or video (VDV);
        a one or more Remote Sensor Devices modules for capturing VDV from an end user;
        code for registering an end user, authorized approvers and contacts of end users and other contacts;
        code for registering information including location coordinates;
    registering an end user;
    registering a contact of end user or other contact;
    registering an authorized approver;
    capturing the voice, data and video of end user;
    displaying voice, data and video of end user on a back-end system;
    displaying voice, data and video of end user on an authorized approver's Telecommunications Device;
    tagging, amending or attaching messages by authorized approver to voice, data and video of end user;
    transmitting by authorized approver the voice, data, video of end user with or without tags, amendments or messages from authorized approver to contacts of end user or to the Telecommunications Devices of contacts of end users or others;

wherein the module, the Telecommunications Device module of end user, the back-end display, the Telecommunications Device of the authorized approver, the Remote Sensor Device (RSD) of the end user, the Telecommunications Devices of the contacts of the end user or other contacts are all operably connected.

2. The system and method of claim 1, wherein the RSD is selected from the group consisting of sensors for: interstitial glucose, blood glucose, ECG, EKG, respiratory rate, pulse, blood pressure, peak flow, push-button alert, spoken alert, or oxygen saturation level.

3. The system and method of claim 1, wherein the VDV are selected from the data from an operably connected RSD, GPS or location or mapping data, voice, images or video.

4. The system and method of claim 1, wherein the VDV is displayed on a back-end system to one or more authorized approvers.

5. The system and method of claim 1, wherein the VDV is displayed on a TD to one or more authorized approvers (AA).

6. The system and method of claim 1, wherein said one or more AA, reviews the VDV and decides to amend, edit or add messages to said VDV.

7. The system and method of claim 1, wherein said one or more AA decides to send said VDV in either original or edited, amended or messaged attached form to one or more contacts of end users or other contacts by way of a single action such as a push button or by way of multiple actions.

8. The system and method of claim 1, wherein the sending of VDV to one or more contacts of an end user or other contact can also begin and open a communication session in which and AA and said contacts are actively engaged by use of either back-end displays or TDs.

9. The system and method of claim 1, wherein said system and method may employ a software application residing on a TD of said user, AA, or contacts that may further reside in a registry file or on a SIM card and may employ the opening and start of said application from a signal sent from said RSD, or a single or multiple action taken on said TD to facilitate said system and method.

10. A system and method for an authorized approver to receive and retransmit voice, data or video (VDV) to contacts of an end user comprising:

providing a module comprising
a graphical user interface for displaying captured voice, data or video objects on a display on a back-end information technology system;
a one or more Remote Sensor Devices (RSD) to capture voice, data, or video (VDV) from an end user;
code for registering an end user, authorized approvers and contacts of end users and other contacts;
code for registering information including location coordinates;
registering an end user;
registering a contact of end user or other contact;
registering an authorized approver;
capturing the voice, data and video of end user;
displaying voice, data and video of end user on a back-end system;
displaying voice, data and video of end user on an authorized approver's Telecommunications Device;
tagging, amending or attaching messages by authorized approver to voice, data and video of end user;
generating alerts, by way of algorithm based on a plurality of factors including but not limited to a user's vital sign data or non-response;
transmitting by authorized approver the voice, data, video of end user with or without tags, amendments or messages from authorized approver for delivery by way of an algorithm, based on a plurality of factors including but not limited to location and expertise to provide intervention, to contacts of end user or to the Telecommunications Devices of contacts of end users or others;
wherein the module, the back-end display, the Telecommunications Device of the authorized approver, the Remote Sensor Device (RSD) of the end user, the Telecommunications Devices of the contacts of the end user or other contacts are all operably connected.

11. The system and method of claim 10, wherein the RSD is selected from the group consisting of a plurality of sensors providing metrics and data for: interstitial glucose, blood glucose, ECG, EKG, respiratory rate, pulse, blood pressure, peak flow, push-button alert, spoken alert, or oxygen saturation level.

12. The system and method of claim 10, wherein the VDV are selected from the data from an operably connected RSD, GPS or location or mapping data, voice, images or video.

13. The system and method of claim 10, wherein the VDV is displayed on a back-end system to one or more authorized approvers.

14. The system and method of claim 10, wherein the VDV is displayed on a TD to one or more authorized approvers (AA).

15. The system and method of claim 10, wherein said one or more AA, reviews the VDV and decides to amend, edit or add messages to said VDV.

16. The system and method of claim 10, wherein said one or more AA decides to send said VDV in either original or edited, amended or messaged attached form to one or more contacts of end users or other contacts by way of a single action such as a push button or by way of multiple actions.

17. The system and method of claim 10, wherein the sending of VDV to one or more contacts of an end user or other contact can also begin and open a communication session in which and AA and said contacts are actively engaged by use of either back-end displays or TDs.

18. The system and method of claim 10, wherein said system and method utilizes a platform comprising data capture, aggregation analytics, and delivery components, wherein said platform resides on a RSD of said user, or on the TD of the AA, or a plurality of contacts that may further reside in a registry file or on a SIM card and may employ the initiation and generation of said application from a signal sent from said RSD, or a single or multiple action taken on said RSD to facilitate said system and method.

* * * * *